(12) United States Patent
Moslehi (10) Patent No.: US 9,423,311 B2
(45) Date of Patent: Aug. 23, 2016

(54) MOVEMENT AND EXPRESSION SENSOR

(71) Applicant: Behzad Moslehi, Los Altos, CA (US)

(72) Inventor: Behzad Moslehi, Los Altos, CA (US)

( * ) Notice: Subject to any disclaimer, the term of this patent is extended or adjusted under 35 U.S.C. 154(b) by 118 days.

(21) Appl. No.: 13/830,344

(22) Filed: Mar. 14, 2013

(65) Prior Publication Data

US 2014/0268099 A1     Sep. 18, 2014

(51) Int. Cl.

| | | |
|---|---|---|
| *G01B 11/16* | (2006.01) | |
| *G01L 1/24* | (2006.01) | |
| *G01K 11/32* | (2006.01) | |
| *A61B 5/11* | (2006.01) | |
| *A61B 5/00* | (2006.01) | |
| *G01K 13/00* | (2006.01) | |

(52) U.S. Cl.
CPC .............. *G01L 1/246* (2013.01); *A61B 5/1107* (2013.01); *A61B 5/1116* (2013.01); *A61B 5/6814* (2013.01); *G01K 11/3206* (2013.01); *G01K 13/002* (2013.01); *A61B 2562/043* (2013.01)

(58) Field of Classification Search
CPC ...................................................... G01B 11/16
USPC ............................................................ 356/32
See application file for complete search history.

(56) References Cited

U.S. PATENT DOCUMENTS

| | | | | | |
|---|---|---|---|---|---|
| 4,937,444 | A | * | 6/1990 | Zimmerman | 250/231.1 |
| 5,399,854 | A | * | 3/1995 | Dunphy et al. | 250/227.17 |
| 5,493,390 | A | * | 2/1996 | Varasi | G01M 11/086 250/227.18 |
| 5,513,913 | A | * | 5/1996 | Ball et al. | 374/120 |
| 5,564,832 | A | * | 10/1996 | Ball et al. | 374/161 |
| 5,649,934 | A | * | 7/1997 | Smeltzer et al. | 606/122 |
| 6,056,436 | A | * | 5/2000 | Sirkis et al. | 374/161 |
| 6,070,269 | A | * | 6/2000 | Tardif et al. | 2/69 |
| 6,072,567 | A | * | 6/2000 | Sapack | 356/32 |
| 6,337,737 | B1 | * | 1/2002 | Chang et al. | 356/32 |
| 6,597,822 | B1 | * | 7/2003 | Moslehi et al. | 385/13 |
| 6,751,367 | B2 | * | 6/2004 | Moslehi et al. | 385/13 |
| 6,895,132 | B2 | * | 5/2005 | Moslehi et al. | 385/13 |
| 7,153,299 | B1 | * | 12/2006 | Tu et al. | 606/15 |
| 7,512,291 | B2 | * | 3/2009 | Mendoza | 385/12 |
| 8,177,702 | B2 | * | 5/2012 | Riehl et al. | 600/13 |
| 8,649,847 | B1 | * | 2/2014 | Park | A61M 25/0158 600/433 |
| 2004/0028310 | A1 | * | 2/2004 | Moslehi et al. | 385/12 |
| 2004/0028311 | A1 | * | 2/2004 | Moslehi et al. | 385/12 |
| 2004/0052444 | A1 | * | 3/2004 | Moslehi et al. | 385/13 |
| 2005/0075704 | A1 | * | 4/2005 | Tu | A61B 18/245 607/88 |
| 2006/0217793 | A1 | * | 9/2006 | Costello | 607/122 |
| 2008/0255629 | A1 | * | 10/2008 | Jenson et al. | 607/19 |
| 2009/0137952 | A1 | * | 5/2009 | Ramamurthy et al. | 604/95.01 |

* cited by examiner

*Primary Examiner* — Roy M Punnoose (74) *Attorney, Agent, or Firm* — File-EE-Patents.com; Jay A. Chesavage (57) ABSTRACT

A movement and expression sensor has a plurality of fiber Bragg gratings (FBG) disposed along the length of an optical fiber, and the optical fiber is placed in contact with a subject's skin surface. The sensors are interrogated for reflected wavelength, which is converted into a temperature or a strain. A series of such measurements can be made to determine the movement or position of the sensor location. A garment may be formed using the sensors and an elastomeric material, such that the sensors may be worn and removed, and the movements of the elastomer in the areas of sensors measured as a wavelength shift to characterize movement or estimate location. The elastomeric garment may be formed as a mask, or a sock, such as for use with a face, or foot.

19 Claims, 6 Drawing Sheets

Figure 1A
Expression Sensors

Figure 1B
Expression Sensors

Figure 1C
Expression Sensors

Figure 2A
Mask Sensors

Figure 2B
Mask Sensors

*Figure 3A*
Body Position Sensor (1st Pos)

*Figure 3B*
Body Position Sensor (2nd Pos)

*Figure 3C*
Body Position Sensor (3rd Pos)

Figure 3D
Body Position Sensor (4th Pos)

| 1 | 2 | 3 | 4  |
|---|---|---|----|
| + | − | + | ++ |

Figure 3E
Body Position Sensor (5th Pos)

| 1 | 2 | 3 | 4 |
|---|---|---|---|
| + | − | − | + |

MOVEMENT AND EXPRESSION SENSOR

FIELD OF THE INVENTION

The present invention is directed to the class of sensors for which multiple measurements can be made using a single strand of fiber having a plurality of sensors fabricated therein. The sensors of the present invention are formed from Fiber Bragg Gratings (FBG), and the sensors may be used to measure any physical phenomenon which can be translated at the sensor into a change in grating pitch, refractive index, or wavelength reflection response over the extent of each FBG sensor, and is directed to detection of these changes using a single optical fiber containing FBGs disposed over the length of the fiber, which is applied to the surface of a human, animal, or plant. In this manner, a change in temperature or strain of each sensor is detectible as a change in wavelength of reflection from the associated FBG sensor.

BACKGROUND OF THE INVENTION

Pattern recognition of facial expression changes are known in the prior art. A typical imaging system captures a sequence of facial expression images and image processing software compares the images, using spatial differences between them to detect and indicate the movement of a particular facial region, such as the use of a video imaging system coupled to pattern recognition software comparing initial images to subsequent ones. In other systems, a facial movement is detected with a motion sensor such as an accelerometer, or other movement sensor.

In certain settings, it may be desirable to characterize the movement and expression of various body surfaces, such as characterizing lip movement for speech recognition, characterization of symmetry of movement for assessment of stroke victim rehabilitation, or to generally make site-specific facial sensor measurements such as temperature or strain.

It is desired to provide an apparatus and method for sensing movement, strain, or temperature in a movable body region, such as a face, foot, arm, leg, or torso.

SUMMARY OF THE INVENTION

An optical fiber having a plurality N of FBG sensors in sequence on the fiber is attached to the surface of a subject using a plurality of individual attachments, one attachment for each grating. The surface for attachment may be a face, a foot, a leg, or any other part of the body which includes a joint or conformable surface where the skin may have a tension or compression increased or reduced from movement of that region. The attachments may be in the form of a worn garment such as a mask, glove, sock, pants, or jacket, or by direct temporary bonding to a skin surface, such as with tape having an embedded sensor, an elastomeric membrane, or an adhesive. The moving region of the body has FBGs placed in individual attachments such as joints or other regions of skin stretching during movement, such that the body movements cause a strain to be developed in the FBG, which strain causes a change in response wavelength which is converted into a joint movement estimate or measured region displacement. A plurality of FBG measurements are taken over time, with the results placed into a memory for comparison with measurements taken at future times, thereby providing the ability to estimate facial expression, foot, or leg position, or any other body positional measurement which may be derived from the stored measurements.

In one example of the invention, the optical fiber and sensors may be captured or molded into a film or conformable mask. In another embodiment of the invention, the optical fiber has a single port, and each FBG sensor operates in a unique range of wavelengths, such that a wavelength interrogator sends out broadband optical energy, which is reflected by each narrowband grating operating in its own wavelength range, thereby providing a measurement of temperature or strain, and the reflected energy returns to the same fiber, where the reflected energy is coupled and applied to a wavelength discriminator, which determines the wavelength of each individual sensor, converting response wavelength associated with each sensor location on the mask into a position or displacement of the wearer of the mask. By comparing the current and previous detected wavelength for each sensor, it is possible to detect a change in sensor strain or temperature, or compare a particular sensor to another sensor, or to itself at a different point in time.

In another embodiment of the invention, a plurality of surface sensors in the form of gratings disposed along a single fiber are applied to a subject or a garment worn by the subject, such as by direct application or embedment in a flexible elastomer which is poured and cured with gratings positioned in suitable locations for estimating a subject's movements, position, or temperature profile. The surface sensors and associated garment may be placed on a foot, arm, leg, or any other part of the body and the recovered sensor data used to estimate the position or temperature of a limb or an appendage. In another embodiment of the invention, the measurements for each sensor are placed into a memory array combined with knowledge of the physical placement of the FBGs, the current measurements are compared to previous measurements, and an estimate a current position estimate is made.

DETAILED DESCRIPTION OF THE INVENTION

Figure 1A:
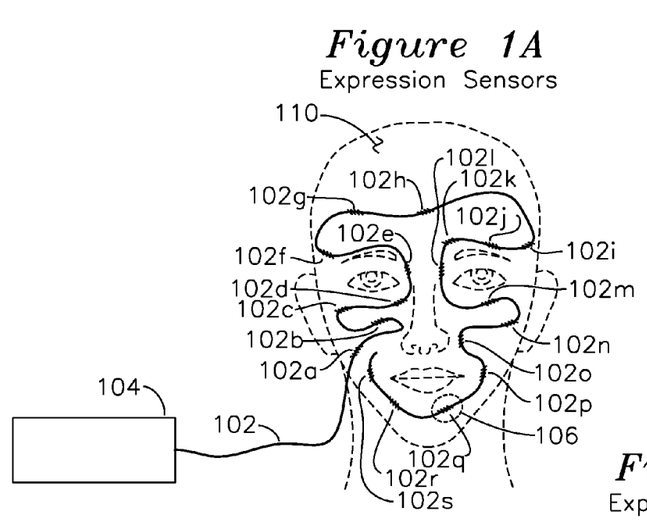
FIG. 1A shows an example of an expression sensor directly applied to a subject.

FIG. 1A shows a subject 110 with a single optical fiber 102 coupled to a wavelength discriminator 104, as will be described. The optical fiber 102 has a plurality of gratings 102a, 102b, 102c, ..., 102s, each grating operating in a unique wavelength range, and reflecting optical energy within a narrowband wavelength of its unique wavelength range, such that the reflected narrowband optical energy from a particular grating will be out of the band of an adjacent optical grating.

Figure 1B:
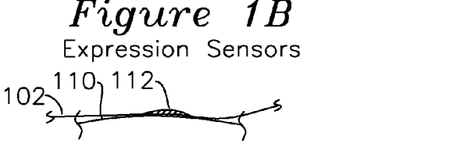
FIG. 1B shows the side view of an expression sensor attachment point.
Figure 1C:
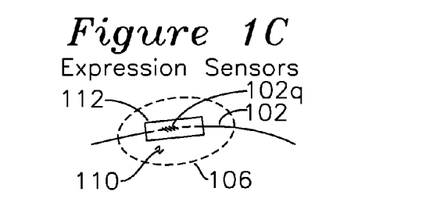
FIG. 1C shows the top view of an expression sensor attachment point.

FIG. 1B shows a side view of a grating attachment, where fiber 102 is attached to subject 110 using a spot adhesive 112 at a sensor site, such as region 106 of FIG. 1A. FIG. 1C shows a top view of region 106, with the attachment performed using an adhesive or tape 112 applied in the region of a grating 102q.

Figure 2A:
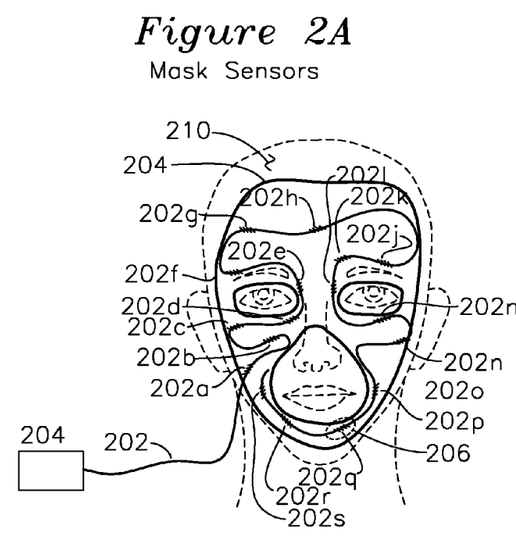
FIG. 2A shows the front view of a sensor mask worn by a subject.
Figure 2B:
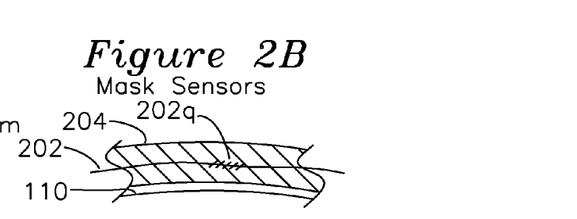
FIG. 2B shows a section view of the sensor mask of FIG. 2A.

FIG. 2A shows an alternative embodiment including a mask 204 applied to a subject 210. The mask has embedded a plurality of FBG sensors 202a, 202b, 202c, . . . , 202s which are formed on a single optical fiber 202, which is embedded in a conformable mask 214, as shown in section 2B, with the locations of sensors corresponding to those of the individual attachments of FIG. 1A. In the embodiments of FIGS. 1A and 2A, each grating 102a, 102b, . . . 102s is placed over a region of facial expression movement such that a movement in a subject 110 face which is coupled to the respective gratings results in a strain applied to a particular FBG sensor 102a, 102b, . . . 102s. For example, a facial expression of happiness may result in an increased strain and greater wavelength reflection response in sensors 102r and 102s, and a facial expression of surprise may result in an increased strain and longer wavelength reflection in sensor 102f and 102i. As each individual sensor 102a . . . 102s accepts optical energy from a broadband source and reflects energy in a particular wavelength band, each sensor is responsive to a unique wavelength (in one embodiment, reflecting a narrow range of wavelengths and passing along to a subsequent sensor all but the reflected narrow band of reflected wavelengths of current and previous sensors), it is possible to determine the specific response wavelength for each sensor, convert that wavelength to a strain value, and, knowing the physical location of the sensor in the mask and associated conversion relationship from strain to position, associate that strain value with a particular mask position or displacement. Additionally, in one embodiment of the invention, the temporal history of wavelength or displacement is maintained in a storage array or table, such that each sensor $\lambda_x$ has an associated array of wavelength values $\lambda_x(t_1), \lambda_x(t_2), \lambda_x(t_3), \ldots, \lambda_x(t_n)$ where $\lambda_x$ is the sensor wavelength at a particular moment in time, and $t_1$, $t_2, t_3, \ldots t_n$, are the particular times the measurements were taken. The wavelength measurements can thereby be taken over time and converted into displacement measurements to provide a mapping of positions over time for each of the individual sensors of the mask 110 or 210.

Figure 3A:
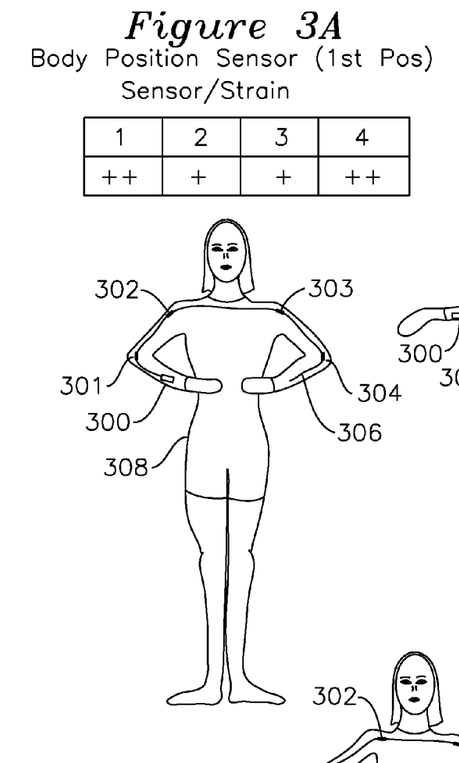
FIGS. 3A, 3B, 3C, 3D, 3E show sensors attached to joints with associated strain for various positions.
Figure 3B:
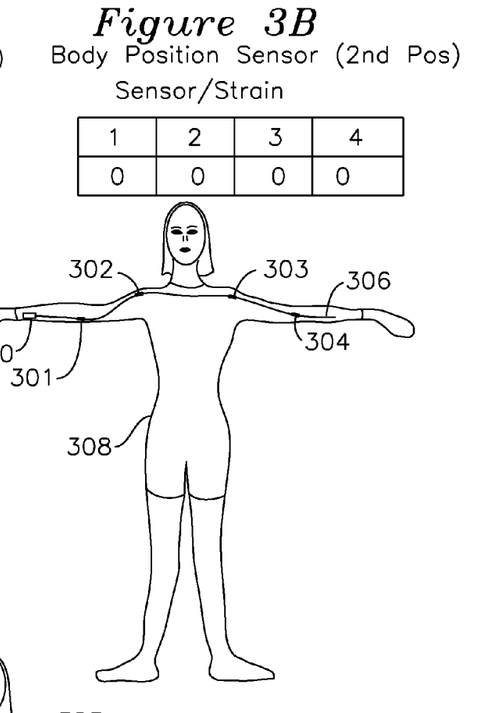
Figure 3C:
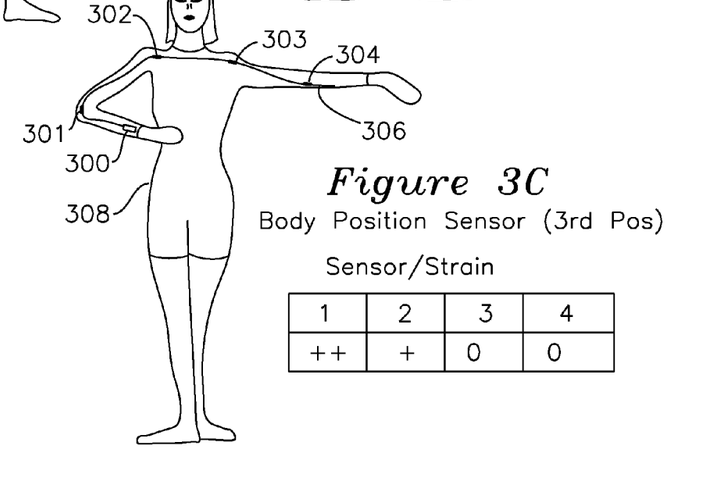
Figure 3D:
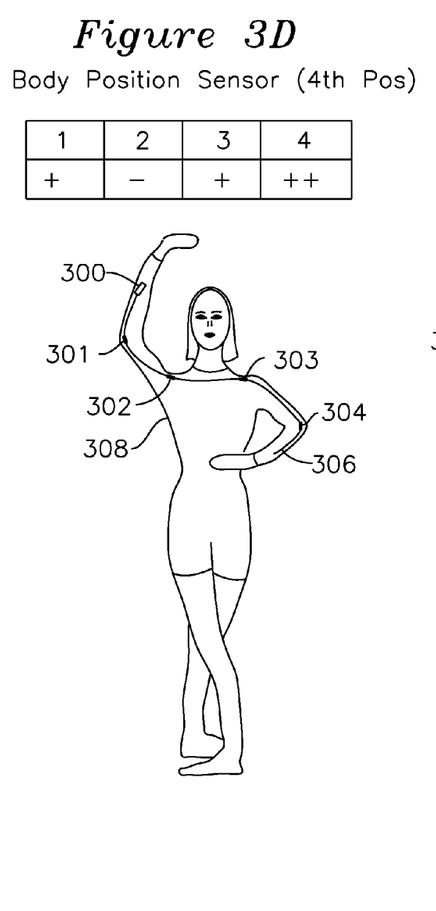
Figure 3E:
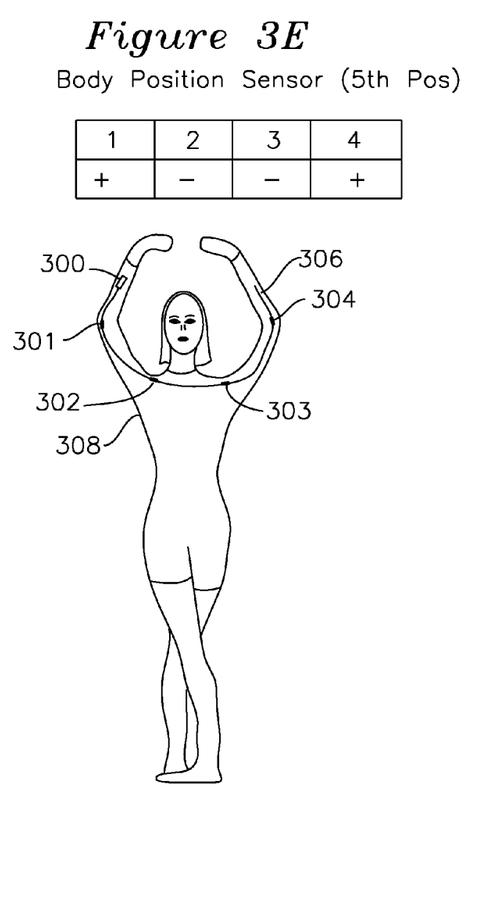

FIGS. 3A, 3B, 3C, 3D, and 3E show a garment sensor worn by a subject in an example which illustrates the use of the system for characterization of ballet dance moves, specifically shown for the arm positions for French school first through fifth ballet positions, corresponding to the positions shown for FIGS. 3A to 3E, respectively. Worn by the subject to be measured in each figure is a garment 308 which includes wavelength interrogator 300, a first joint sensor 301 attached to a skin surface near an elbow, a second joint sensor 302 attached to a skin surface near a shoulder, a third joint sensor attached to a skin surface near an opposing shoulder 303 and a fourth joint sensor 304 attached to a skin surface near an opposite elbow, with each sensor 301, 302, 303, 304 affixed to the skin such as with wearable garment 308 or by direct attachment means as was described in FIG. 1B, 1C, or 2B. Each sensor 301, 302, 303, 304 is placed to provide information about the tension or compression of the skin surface, such that joint position may be estimated. Each of the FIGS. 3A through 3E includes a corresponding table indicating the amount of strain associated with each sensor, such that sensor 1 (FBG 301), sensor 2 (FBG 302), sensor 3 (FBG 303), and sensor 4 (FBG 304) each are respectively stretched or compressed during movement, and those movements are associated with the positions shown. For example, in FIG. 3A, sensors 1 and 4 associated with elbow movement have a maximum strain associated with tensioning of the garment outside the elbows (indicated by ++ and corresponding to a large reflected wavelength shift downwards), whereas the shoulder sensors 2 and 3 experience only minor strain (indicated by + and corresponding to a small reflected wavelength shift downwards). In FIG. 3B, corresponding to French ballet second position, all sensors experience neutral strain, indicated as "0" in the associated table, and resulting in no wavelength shift. FIGS. 3C, 3D, and 3E show corresponding sensor strains associated with the ballet positions shown.

Figure 4:
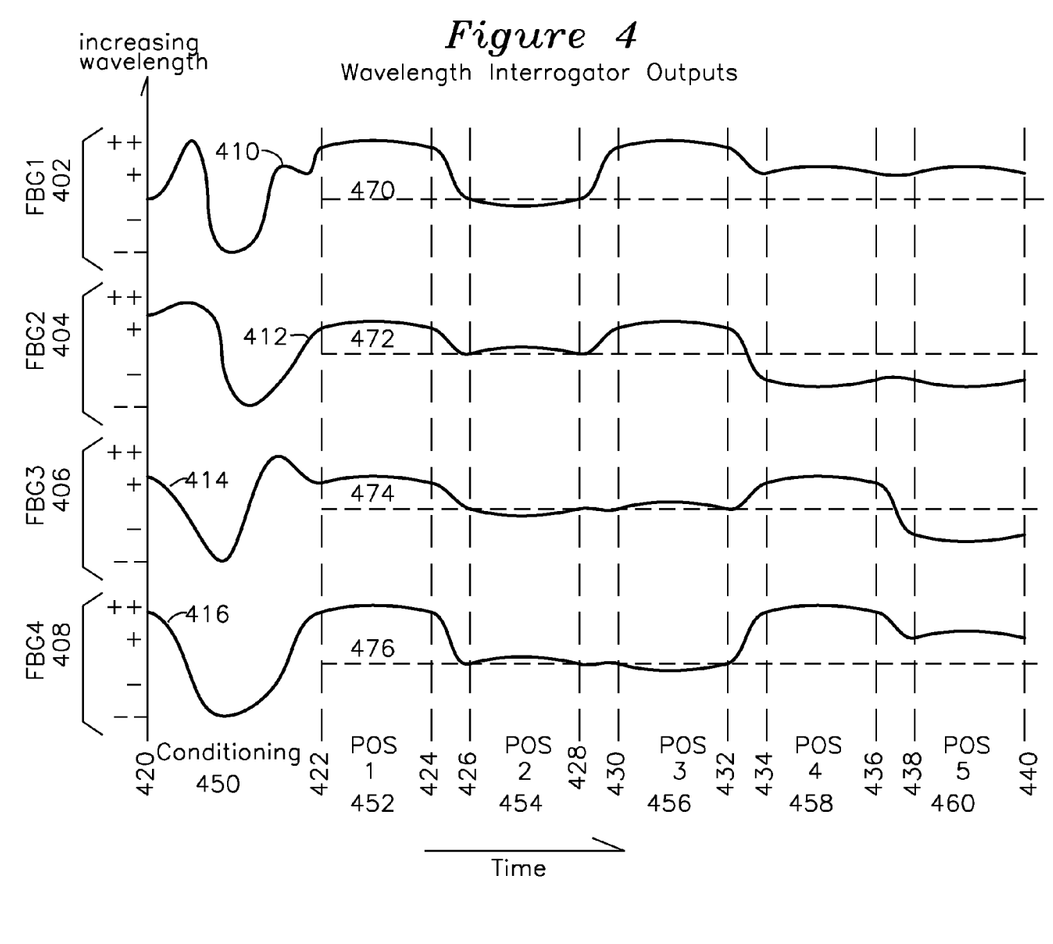
FIG. 4 is a plot of temporal reflected wavelengths associated with the joint movements shown for FIG. 3A, 3B, 3C, 3D, and 3E.

FIG. 4 shows a plot of reflected wavelengths as might be generated by a wearer of the garment 308 shown in FIG. 3A and provides for a method of decoding position from reflected FBG wavelengths as determined by wavelength interrogator 300 of FIG. 3A through 3E. In one example embodiment, the garment 308 includes FBG strain sensors 301, 302, 303, and 304 as shown in FIGS. 3A through 3E, and a wearer of the garment moves through a range of motions during a conditioning interval 450, during which interval the FBG corresponding sensors FBG1, FBG2, FBG3, and FBG4, respectively, and corresponding to sensors 1 through 4, respectively, reflect optical energy in each FBG range of wavelengths 402, 404, 406, and 408, respectively. After the conditioning interval from 420 to 422, the FBG center wavelengths 470, 472, 474, and 476 for each sensor are determined and used thereafter to estimate relative positions (++, +, 0, −, and −−) from interrogator reported wavelength shifts, which are proportional to sensor strain and limb position, as was described previously. During interval 452, the wavelength interrogator detects an FBG wavelength set comprising {++,+,+,++} which is associated with wavelength shifts for position 1 shown in FIG. 3A.

In a subsequent interval 454, the wavelength interrogator detects the wavelength set {0,0,0,0} corresponding to position 2 shown in FIG. 3B. Similarly, during intervals 456, 458, and 460, the wavelength interrogator detects wavelengths sets {++,+,0,0}, {+,−,+,++}, and {+,−,−,+}, corresponding to the positions shown in FIGS. 3C, 3D, and 3E, which may be then associated with the corresponding associated arm positions.

While estimation of arm positions are shown by way of example in FIGS. 3A through 3E and FIG. 4, this may be extended to include detection and real-time estimation of joint position for the legs, hips, feet, or any articulating joint or body member.

In another embodiment of the invention, the sensors may be attached to plants using an adhesive or other binding material to measure deflection or strain on various parts of a plant. For example, a binding agent which does not interfere with plant leaf transpiration or other surface plant cell functionality may be applied to the leaf or branch surface to form a movement or long term growth sensor.

Figure 5:
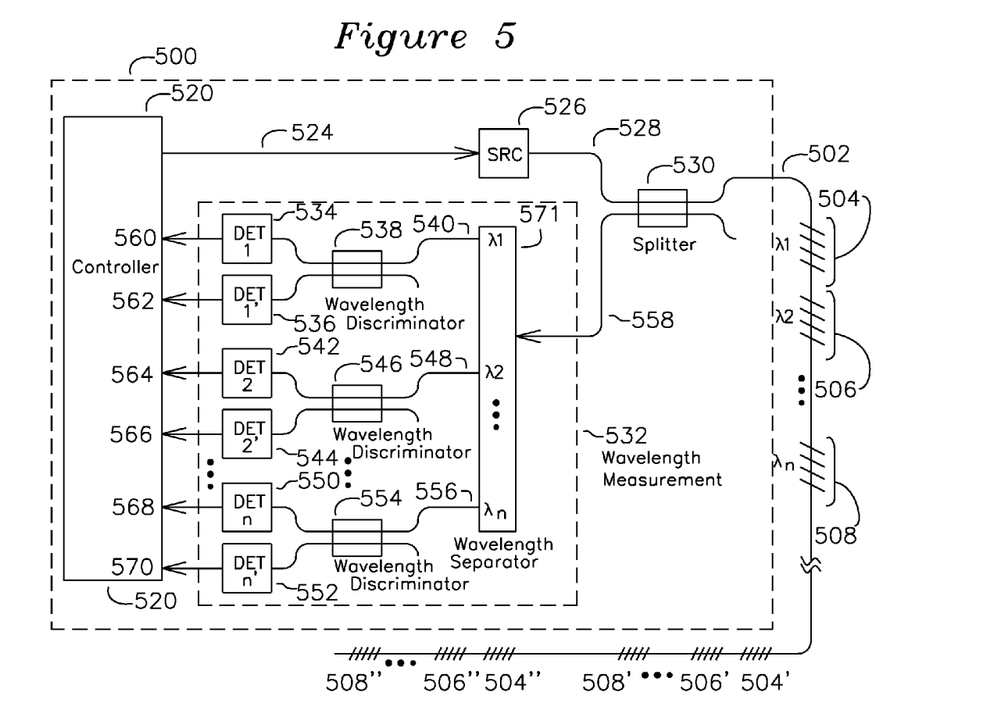
FIG. 5 shows a block diagram for a wavelength discriminator, as used by a strain and temperature measurement system.

FIG. 5 shows a strain/temperature measurement system 500 attached to a fiber 502 comprising a plurality of gratings 504, 506, and 508 corresponding to the plurality of sensors 102a . . . 102s of FIG. 1A and plurality of sensors 202a . . . 202s of FIG. 2A. A broadband source 526 is applied via fiber 528 to splitter 530, which sends optical energy to sensor array 502, which is a single fiber having a plurality of gratings 504, 506, through 508 fabricated along the length of the fiber. There may be an arbitrary number of such gratings, and each grating is responsive to and reflects a unique narrowband set of wavelengths $\lambda_1$, $\lambda_2$, through $\lambda_n$. The gratings 504, 506, through 508 return this narrowband optical energy at a response wavelength specific to each grating characteristic, thereby sensing mechanical changes in the grating associated with temperature or strain at each grating, and these reflected optical signals are directed by splitter 530 to wavelength measurement device 532, which may be any system for discriminating a plurality of wavelengths. In the wavelength measurement system 532 shown, the incoming reflected optical energy is sent to a wavelength separator 571, which performs coarse separation of wavelength, and this is followed by wavelength discriminators 538, 546, 554, which have a sine characteristic for a given wavelength, forming complementary outputs and splitting the complementary optical output between detector 1 534 and detector 1' 536 to controller 520 analog complementary inputs 560 and 562. This same system of complementary wavelength discriminators is used for each incoming wavelength channel, comprising discriminators 546 for channel 2 complementary detectors 542 and 544 coupled to controller inputs 564 and 566, and for channel n, wavelength discriminator 554 coupled to complementary detectors 550 and 552 driving controller inputs 568 and 570. For each grating wavelength, there is a corresponding input detector pair which uses power ratio to determine wavelength.

Figure 6:
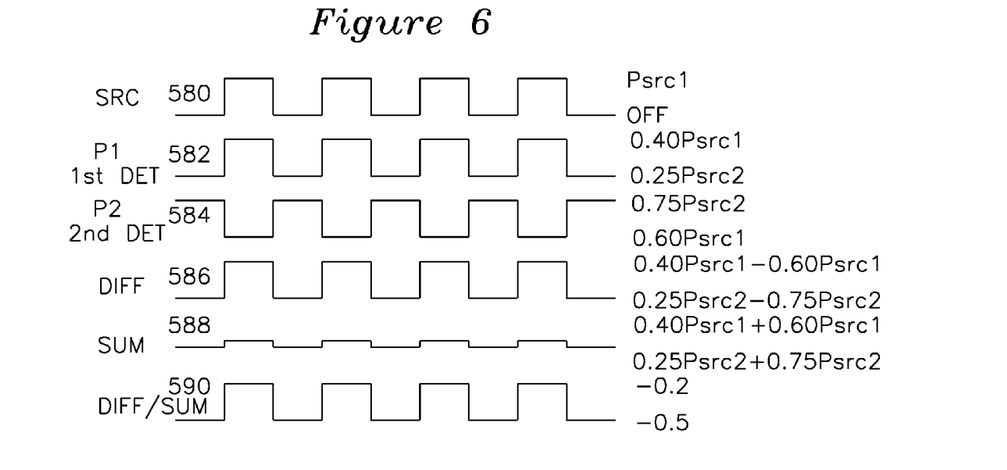
FIG. 6 shows waveforms of the wavelength discriminator of FIG. 5.

FIG. 6 shows example waveforms of operation, including those of the broadband source 526 of FIG. 5, which is controlled by a signal 580 causing the broadband source 526 of FIG. 5 to be commutated on and off. Each of the detector pairs responding to a sensor grating reflecting optical power at a wavelength produces an output and a complementary output, shown as signals 582 and 584 which may be the signal outputs of exemplar detectors 534 and 536, or any of the other detector pairs. These signals are summed in signal 588 and subtracted from each other in signal 586. The ratio of the sum and difference signal may be used to form a computation shown as signal 590 which may be applied to a lookup table, or any mathematical relationship which can be used to determine the wavelength of the reflected optical energy. In this manner, a plurality of optical sensors operating in unique wavelength ranges returns a plurality of unique specific sensor wavelengths which are applied to a particular set of detectors, the output being resolved by measurement device 532 of FIG. 5 by using power ratios, or any other suitable means for wavelength detection. During the time the optical source 526 is off, the detector and system analog offsets are determined, and when source 526 is on, the detector pair for each wavelength channel determines the actual wavelength from the difference divided by the sum separately for each detector pair forming a wavelength channel.

In one embodiment of the invention, the reflected wavelength response of each grating 504, 506 . . . 508 is selected to operate in a unique band of wavelengths from other gratings, and with the gratings having a high reflectivity, such that the majority of the optical energy from each grating is reflected at a wavelength indicating the strain or temperature of that grating. By placing each grating in a unique wavelength range of operation, one grating does not "shadow" another grating on the fiber sensor, and all sensor gratings 504, 506, . . . , 508 of the optical fiber are continuously illuminated by source 526. In this embodiment, the wavelength separator 571 separates each associated band of reflected grating wavelengths for delivery to each discriminator 538, 546, 554, which converts the measured reflected wavelength into a strain, a temperature, or local measurement for use in compensating a strain measurement, and the strain measurement subsequently converted to deflection or position according to well known methods in strain sensing.

The surface measurement system described in the figures and specification may be used for many different purposes. A human or animal subject may be fitted with sensors or a sensor garment, and facial expressions, arm and leg movements, including sensing of the position of the feet, fingers and toes, may be characterized and stored in memory for comparison in past and future measurement sessions by examining previously stored copies of the measurements to discern differences in measurements from one session to another, or for comparison of measurements within a particular single session. The series string of sensors may be formed into an elastomeric garment for use as a mask, glove, or sock. FBG sensors which measure strain may be placed adjacent to FBG sensors which are shielded from strain and measure temperature only, which temperature may be used to compensate for temperature dependencies in adjacent FBG strain sensors. The FBG sensors may be embedded in an elastomer formed into a garment, or the elastomeric garment may be formed by securing the sensors to the desired measurement areas of a subject and thereafter applying an elastomer such as a quick-cure elastomer, or by first making a mold of the subject region of interest and making the elastomeric garment by applying it to the mold so created.

Figure 7:
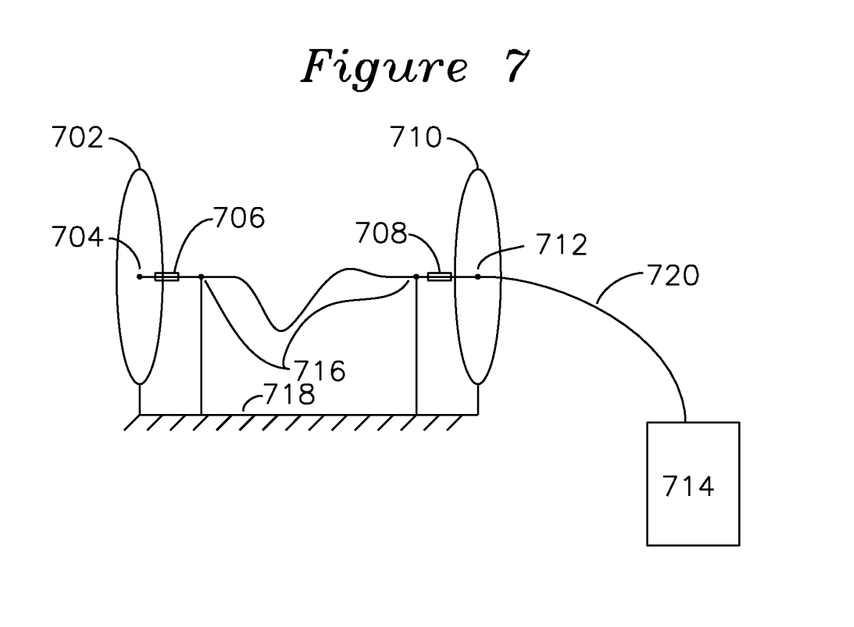
FIG. 7 is a diagram for an all-optical acoustic sensor.

In another embodiment of the invention shown in FIG. 7 and which may be used separately or in combination with the previously described examples of body sensing, one or more FBG sensors is coupled to a diaphragm such that acoustic energy is coupled to the diaphragm, resulting in a strain variation in the optical fiber, which is transmitted as an optical signal, and subsequently wavelength demodulated, such as with the wavelength interrogator described in FIGS. 5 and 6. For the demodulation of a steady state signal with primarily an AC component such as acoustic waves, the commutating shown in FIG. 6 may not be necessary, and the differential detector outputs may be read directly and continuously, with source waveform 580 applied continuously, rather than commutated to compensate for DC errors as shown. FIG. 7 describes the acoustic demodulator case for two FBG sensors 706 and 708, which are each coupled to diaphragms 702 and 710, respectively, each of which diaphragm has an outer perimeter which is anchored to a fixed base 718 and have central points 704 and 712, respectively, which couple acoustic wave energy to the sensors 706 and 708, respectively. The opposite ends of the FBG sensors 706 and 708 are also anchored 716, with the fiber also passing through diaphragm attachment point 712 through optical fiber 720 to wavelength interrogator 714, which provides broadband illumination and converts wavelength shifts from reflected optical energy from FBG 706 and 708 into an analog or digital signal, as was described for FIGS. 5 and 6. In this manner, acoustic energy which strikes diaphragms 702, 710, is converted to instantaneous strains by FBG sensors 706 and 708, and returned as an estimated signal. The diaphragms 702 and 710 may be coupled to directional acoustic waveguides, for example, to imitate the behavior or human or animal hearing.

Alternatively, the sensors may be embedded into a conformable generic or special purpose elastomeric sheet which is placed in contact with a subject for measurement and characterization of movement, surface strain, or temperature, or any combination of these. The sensors may be formed as in-fiber FBGs with each of the N sensors operating in its own wavelength, or each of these may be used in a sensor segment having N individual sensors, each operative in a unique wavelength as described.

In one example embodiment as was described in FIGS. 5 and 6, N sensors, each operating in a unique range of wavelengths, may be coupled to each other in a series arrangement.

A broadband source is applied, and each sensor is examined for a reflected wavelength, which is resolved to a position.

In another example embodiment where M×N sensors are required, each of the N sensors operates in a unique wavelength range as previously described, but M such strings of N sensors are arranged in a repeating sequence. Ordinarily, this would cause interference and inability to discriminate between each of the M sensors operating in a particular wavelength band, but for this particular repeated sensor configuration, the broadband source is pulsed at a rate no greater than the time of flight through the entire string of M×N sensors, with each string of sensors read during an associated time-of-flight time window. In this manner, the broadband source is pulsed once, and in successive time intervals, each of the M strings of sensors returns N wavelengths are resolved, such that the first set of N sensors is read in a first time interval, the second set of sensors are read in a second interval, and the process repeats until the last string of N sensors is read in its respective time interval, after which the process repeats with the next pulse of broadband optical energy. The maximum interrogation rate is governed according to the time-of-flight return time for all of the sensors sensor, thereby forming an array of M×N sensors for use in the present invention.

I claim:

1. A surface measurement system comprising:
   a single optical fiber having a plurality N of fiber Bragg gratings (FBG) formed in the optical fiber, each said FBG forming an optical sensor for placement on a surface area of a subject, at least one said FBG coupled to a particular surface of a subject and responsive to a strain of said surface, thereby reflecting incident optical energy in a unique band of wavelengths which are distinct from the wavelengths reflected by other gratings on said optical fiber, a wavelength of said reflected optical energy indicating a strain of the associated said surface, said optical fiber having an optical port for the introduction and removal of optical energy;
   a wavelength interrogator comprising:
      a broadband optical source coupled to provide optical energy to said optical port;
      wavelength separation means for receiving optical energy which is reflected in unique wavelengths by said plurality of FBGs and directing said optical energy to a particular detector;
      said detector converting an optical response to a measurement of strain;
   said strain being resolved to a positional movement of a region associated with said sensor;
   said wavelength interrogator comparing an initial strain measurement to a subsequent strain measurement, thereby resolving a new position of a region associated said sensor.

2. The surface measurement system of claim 1 where said optical sensors include adhesions for application to the skin or surface of a subject.

3. The surface measurement system of claim 1 where said optical sensors include tape for application to the skin or surface of a subject.

4. The surface measurement system of claim 1 where said optical sensors are embedded into an elastomer which is applied to a subject, whereby movement of a subject skin surface in a particular area is coupled to an associated FBG.

5. The surface measurement system of claim 1 where said wavelength interrogator initial strain is stored in a wavelength interrogator memory.

6. The surface measurement system of claim 5 where at least one of said FBG sensors is responsive to an ambient temperature to compensate for the measured strain in a different FBG sensor.

7. The surface measurement system of claim 1 where said resolution of a new position is the resolution from a jointed region of a surface.

8. The surface measurement system of claim 1 where said plurality of said optical sensors are in particular positions and orientations, the plurality of optical sensors providing respective reflected wavelength shifts and thereby indicating a change in position or displacement of regions derived from said change in strain of said particular positions and orientations in a surface of a subject.

9. The surface measurement system of claim 8 where said position or displacement derived from said change in strain indicates a change in position of at least one of: a subject's face, a subject's fingers, a subject's limbs, a subject's legs, or a subject's feet.

10. The surface measurement system of claim 1 where said physical change is a strain generated by said optical sensors affixed to at least one of:
    an animal, or a human, said physical change estimating a joint position or surface movement;
    plant, said physical change estimating a movement or long term growth pattern.

11. The surface measurement system of claim 1 where said placement on a surface area of a subject is placement on at least one of: a wearable garment, a face mask, a body suit, or a glove.

12. A method of movement detection forming temporal measurements from a measurement system comprising:
    a single optical fiber having a plurality N of fiber Bragg gratings (FBG) formed in the optical fiber, each said FBG for placement on a surface area of a subject and coupled to displacements and strains of said surface area, said surface area selected to provide positional location from an associated measured strain after deflection and in comparison with an initial strain associated with an initial position, each FBG reflecting incident optical energy in a unique band of wavelengths which are distinct from the wavelengths reflected by other gratings on said optical fiber, said optical fiber having an optical port for the introduction and removal of optical energy;
    a wavelength interrogator comprising:
       a broadband optical source coupled to provide optical energy to said optical port;
       wavelength separation means for receiving optical energy which is reflected in unique wavelengths by said plurality of FBGs and directing said optical energy to a particular detector;
       said detector converting an optical response to a measurement of temperature or strain;
    the method of movement detection comprising:
    establishing a baseline reflected wavelength measurement for each said FBG sensor associated with said initial position;
    determining a displacement or movement based on a change in reflected wavelength of each said FBG sensor compared to said baseline wavelength measurement and said initial position;
    determining a new position which is derived from said determining a displacement or movement in combination with said FBG sensor positions on a subject.

13. The method of claim 12 where said displacement and strains of said surface area are coupled to said FBG sensors positioned on a wearable garment and said position estimation step utilizes the location of said FBG sensors on said wearable garment in combination with a reflected wavelength from said FBG sensor to determine a position of said garment.

14. The method of claim 12 where said FBG sensors are attached to a subject using an adhesive.

15. The method of claim 12 where said baseline establishment step utilizes a range of wavelength responses to determine a rest position.

16. A surface measurement system for estimation of the position or displacement of a conformable surface, the measurement system having:

an optical fiber having a plurality of Fiber Bragg Gratings (FBG), each said FBG coupled to said conformable surface, at least one said FBG coupled to a region of compression or expansion of said conformable surface, said plurality of FBGs oriented on said conformable surface to estimate a movement position of said conformable surface;

where each of said FBGs is operative in a unique range of wavelengths, each said FBG reflecting optical energy in a particular one of said unique range of wavelengths;

said optical fiber coupled to a wavelength interrogator for exciting said plurality of FBG with broadband optical energy, said wavelength interrogator converting reflected optical energy from each said FBG into a strain or a temperature measurement;

where each said strain or temperature measurement from each said FBG, in combination with the positional location of each said FBG, and an initial strain from each said FBG, provides an estimate of the position or displacement of said conformable surface.

17. The surface measurement system of claim 16 where said FBGs are positioned in a glove coupled to the FBGs of said conformable surface.

18. The surface measurement system of claim 16 where said FBGs are positioned in a body suit coupled to the FBGs of said conformable surface.

19. The surface measurement system of claim 16 where said FBGs are positioned in a wearable face mask coupled to the FBGs of said conformable surface.

* * * * *